United States Patent [19]

Goold et al.

[11] Patent Number: 5,840,870
[45] Date of Patent: Nov. 24, 1998

[54] POLYNUCLEOTIDES PANC1A AND PANC1B ASSOCIATED WITH PANCREATIC CANCER

[75] Inventors: Richard D. Goold, San Francisco; Ingrid E. Akerblom, Redwood City; Jeffrey J. Seilhamer, Los Altos Hills, all of Calif.

[73] Assignee: Incyte Pharmaceuticals, Inc., Palo Alto, Calif.

[21] Appl. No.: 581,240

[22] Filed: Dec. 29, 1995

[51] Int. Cl.[6] ............................ C12N 15/11; C12N 15/66; C12N 15/85; C07H 21/04

[52] U.S. Cl. ........................... 536/23.5; 536/24.33; 435/6; 435/240.1; 435/320.1; 935/6; 935/9; 935/11; 935/77; 935/78; 514/44

[58] Field of Search ................................. 536/23.1, 24.1, 536/23.5, 24.5, 24.33, 24.31; 435/6, 91.2, 240.1, 320.1; 514/44; 935/6, 7, 77, 78, 9, 11

[56] References Cited

PUBLICATIONS

Dryja et al. Journal of Cell Biology 95:218a Abstract 10039, (1982).

Fischer et al. Genomics 21:525–537 (Jun. 1994).

Sambrook et al. eds. Molecular Cloning: A Laboratory Manual Cold Spring Harbor Press New York (1989) pp. 3.5–3–26.

Schutte, M et al., "An Integrated High–Resolution Physical Map of the DPC/BRCA2 Region at Chromosome 13q12[1]" *Cancer Research* 55(20):4570–4574 (1995).

Auffray, C et al., "IMAGE: molecular integration of the analysis of the human genome and its expression" *C R Acad Sci III* 318(2):263–272 (1995).

Hillier et al. (Direct Submission), GenBank Sequence Database (Accession H95240), National Center for Biotechnology Information, National Library of Medicine, Bethesda, Maryland 20894.

Couch, FJ et al., "Generation of an integrated transcription map of the BRCA2 region on chromosome 13q12–q13" *Genomics* 36(1):86–99 (1996).

Caldas et al., "Frequent somatic mutations and homozygous deletions of the p16 (MTS1) gene in pancreatic adenocarcinoma," *Nature Genetics*, 8:27–32 (Sep. 1994).

Schutte et al., "Identification by representational difference analysis of a homozygous deletion in pancreatic carcinoma that lies within the BRCA2 region," *Proc. Natl. Acad. Sci. USA*. 92:5950–5954 (Jun. 1995).

Lisitsyn et al., "Comparative genomic analysis of tumors: Detection of DNA losses and amplification," *Proc. Natl. Acad. Sci. USA*, 92:151–155 (Jan. 1995).

Mueller–Pillasch et al., "Differential gene expression in pancreatic cancer. Use of an automated approach for the large scale isolation and characterisation of cDNA clones containing differentially expressed sequences," *Unpublished* (Aug. 1994) GI 533948 –Abstract only.

*Primary Examiner*—W. Gary Jones
*Assistant Examiner*—Debra Shoemaker
*Attorney, Agent, or Firm*—Incyte Pharmaceuticals, Inc.; Barbara J. Luther; Lucy J. Billings

[57] ABSTRACT

The present invention provides polynucleotide sequences designated PANC1A and PANC1B which are associated with a genomic sequence related to pancreatic cancer as well as other cancers. The present invention also provides for PANC1A and PANC1B antisense molecules. The invention further provides genetically engineered expression vectors and host cells for the production of purified PANC1A and PANC1B polypeptide; antibodies, antagonists and inhibitors of PANC1A and PANC1B polypeptide; and pharmaceutical compositions and methods of treatment based on the polypeptide, its antibodies, antagonists and inhibitors. The invention specifically provides for use of the polypeptide as a diagnostic composition for the detection of pancreatic cancer in individuals at risk for and subject to pancreatic cancer. The invention also relates to therapeutic methods and compositions based upon the nucleotide sequences for PANC1A and PANC1B.

10 Claims, 16 Drawing Sheets

```
GTACGGAGGT GAGGTTTGTN ACCGCGATTC TAAGAGGTGG GCTTTTAGTC CCTCCAGACC    60
TCGGCTTTAG TGCTGTCTCC GCTTTTYTTT CACCTTCACA GAGGTTCGTG TCTTCCTAAA   120
AGAAGGTTTT ATTGGGAGGT AAAGGTCAAT GCGTAGGGGT AGAGTAAGAT GTCTTATGGT   180
GAAATTRAAG GTAAATTCTT GGGACCTAGA GAAGAAGTAA CGAGTGAGCC ACGCTGTAAA   240
AAATTGAAGT CAACCACAGA GTCGTATGTT TTTCACAATC ATAGTAATGC TGATTTTCAC   300
AGNATCCAAG AGAAAACTGG AAATGATTGG GTCCCTGTGN NCATCATTGA TGTCAGAGGA   360
CATAGTTATT TGC                                                     373
```

```
GTACGGAGGT GAGGTTTGTN ACCGCGATTC TAAGAGGTGG GCTTTTAGTC CCTCCAGACC   60
TCGGCTTTAG TGCTGTCTCC GCTTTTYTTT CACCTTCACA GAGGTTCGTG TCTTCCTAAA  120
AGAAGGTTTT ATTGGGAGGT AAAGGTCAAT GCGTAGGGGT AGAGTAAGAT GTCTTATGGT  180
GAAATTRAAG GTAAATTCTT GGGACCTAGA GAAGAAGTAA CGAGTGAGCC ACGCTGTAAA  240
AAATTGAAGT CAACCACAGA GTCGTATGTT TTTCACAATC ATAGTAATGC TGATTTTCAC  300
AGNATCCAAG AGAAAACTGG AAATGATTGG GTCCCTGTGN NCATCATTGA TGTCAGAGGA  360
CATAGTTATT TGC                                                    373
```

FIG. 1

```
GTGAGGTTTG TTACCNCGAT TCTGAGAGGT GGGCTTTTAG TCCCTCCAGA CCTCGGCTTT    60
AGTGCTGTCT CCGMTTTTCT TTCACCTTCA CAGAGATGTC TTATGGTGAA ATTGAAGGTA   120
AATTCTTGGG ACCTAGWGAA GAAGTAACGA GTGAGCCACG CTGTAAAAAA TTGAAGTCAA   180
CCACAGAGTC GTATGTTTTT CACAATCATA GTAATGCTGA TTTTCACAGW ATCCAAGAGA   240
AAACTGGAAA TGATTTGGGT CCCTGTGACC ATCATTNATG TCAGAGGNCA TAGTTAATTT   300
GCAGGAGANC AAAAATCAAA A                                             321
```

FIG. 2

```
       1                                                              50
20483  ........GT GAGGTTTGTT ACCnCGATTC TGAGAGGTGG GCTTTTAGTC
71178  GTACGGAGGT GAGGTTTGTn ACCGCGATTC TAAGAGGTGG GCTTTTAGTC
  XS7  .......... .......... ..TCGACCCA CGCGTCCGGG GCTTTTAGTC 51                                                            100
20483  CCTCCAGACC TCGGCTTTAG TGCTGTCTCC GNTTTTCTTT CACCTTCACA
71178  CCTCCAGACC TCGGCTTTAG TGCTGTCTCC GCTTTTNTTT CACCTTCACA
  XS7  CCTCCAGACC TCGGCTTTAG TGCTGTCTCC GCTTTTCTTT CACCTTCACA 101                                                           150
20483  G......... .......... .......... .......... ..........
71178  GAGGTTCGTN TCTTCCTAAA AGAAGGTTTT ATTGGGAGGT AAAGGTCAAT
  XS7  GAGGTTCGTG TCTTCCTAAA AGAAGGTTTT ATTGGGAGGT AAAGGTCAAT 151                                                           200
20483  .......... ......AGAT GTCTTATGGT GAAATTGAAG GTAAATtcTT
71178  GCGTAGGGGT AGAGTAAGAT GTCTTATGGT GAAATTrAAG GTAAATTCTT
  XS7  GCGTAGGGGT AGAGTAAGAT GTCTTATGGT GAAATTGAAG GTAAATTCTT 201                                                           250
20483  GGGACCTAGN GAAGAAGTAA CGAGTGAGCC ACGCTGTAAA AAATTGAAGT
71178  GGGACCTAGA GAAGAAGTAA CGAGTGAGCC ACGCTGTAAA AAATTGAAGT
  XS7  GGGACCTAGA GAAGAA.... .......... .......... ..........

251                                                           300
20483  CAACCACAGA GTCGTATGTT TTTCACAATC ATAGTAATGC TGATTTTCAC
71178  CAACCACAGA GTCGTATGTT TTTCACAATC ATAGTAATGC TGATTTTCAC
  XS7  .......... .......... ...CACAATC ATAGTAATGC TGATTTTCAC 301                                                           350
20483  AGNATCCAAG AGAAAACTGG AAATGATTTG GGTCCCTGTG ACCATCATTN
71178  AGNATCCAAG AGAAAACTGG AAATGA.TTG GGTCCCTGTG NNCATCATTG
  xs7  AGAATCCAAG AGAAAACTGG AAATGA.TTG GGTCCCTGTG ACCATCATTG 351                                                           400
20483  ATGTCAGAGG NCATAGTTAA TTTGCAGGAG ANCAAAAATC AAAA......
71178  ATGTCAGAGG ACATAGTTAT TT*GC..... .......... ..........
  XS7  ATGTCAGAGG ACATAGTTAT TT*GCAGGAG AACAAAATCA AAACTACAGA 401                                                           450
20483  .......... .......... .......... .......... ..........
71178  .......... .......... .......... .......... ..........
  XS7  TTTGCATAGAC CTTTGCATGA TGAGATGCCT GGTAATAGAC CAGATGTTA 451                    487
20483  .......... .......... .......... ........
71178  .......... .......... .......... ........
  XS7  TTGAATCCATT GATTCACAGG TTTTACAGGA AGCACGT
```

FIG. 3

```
              10         20         30         40         50         60
              |          |          |          |          |          |
[071178] 071178.As... GTACGGAGGTGAGGTTTGTnACCGC-GATTCTaAGAGGTGGGCTTTtAGTCCCTCCAGAC

[071178] 071178  -> GTACGGAGGTGAGGTTTGTNACCGC-GATTCTAAGAGGTGGGCTTTAGTCCCTCCAGAC
[180773] 180773  ->                          CCGCNGATTCTAAGAGAGGTGGGCTTTNAGTCCCTCCANAC
[496071] 496071  ->                              CCGC-GATTCTGAGAGGTGGGCTTTTAGTCCCTCCAGAC 70         80         90         100        110        120
              |          |          |          |          |          |
[071178] 071178.As... CTCGGCTTTAGTGCTGTcTCCgcTTTTyTTTCACCTTCACAGAGGTTCGTgTcTTCCtAA

[071178] 071178  -> CTCGGCTTTAGTGCTGCTGTNTCCNNTTTTTTTCACCTTCACAGAGGTTCGTTTNTTCCNAA
[180773] 180773  -> CTCGGCTTTAGTGCTGCTGTCTCCGCTTTTNTTTCACCTTCACAGAGGTTCGTGTCTTCCTAA
[496071] 496071  -> CTCGGCTTTAGTGCTGCTGTCTCCGNTTTCTTTCTTTCACCTTCACAGAGGTTCGTGTCTTCCTAA 130        140        150        160        170        180
              |          |          |          |          |          |
[071178] 071178.As... AAGAAGGTTTTATTGGGAGGTAAAGGTCAATGCGTAGGGGTAGAGTAAGAATgTCTTATGG

[071178] 071178  -> AAGAAGGTTTTATTGGGAGGTAAAGGTCAATGCGTAGGGGTAGAGTAAAATNTNTTATG
[180773] 180773  -> AAGAAGGTTTTATTGGGAGGTAAAGGTCAATGCGTAGGGGTAGAGTAAGATGTCTTATGG
[496071] 496071  -> AAGAAGGTTTTATTGGGAGGTAAAGGTCAATGCGTAGGGGTAGAGTAAGATGTCTTATGG
```

FIG. 4A

[071178] 071178.As... TGAAATTrAAGGTAAATTCTTGGGACCTAGAGAAGAAGTAACGAGTGAGCCACGCTGTAA

[180773] 180773 -> TGAAATTAAAGGTAAATTCTTGGGACCTAGAGAAGAAGTAACGAGTGAGCCACG
[496071] 496071 -> TGAAATTGAAGGTAAATTCTTGGGACCTAGAGAAGAAGTAANGAGTGAGCCACGCTGTAA

[071178] 071178.As... AAAATTGAAGTCAACCACAGAGTCGTATGTTTTCACAATCATAGTAATGCTGATTTTCA

[496071] 496071 -> AAAATTGAAGTCAACCACAGAGTCGTATGTTTTCACAATCATAGTAATGCTGATTTTCA

[071178] 071178.As... CAGnATCCAAGAGAAAACTGGAAATGATTGGGTCCCTGTGnnCATCATTGATGTCAGAGG

[496071] 496071 -> CAGNATCCAAGAGAAAACTGGAAATGATTGGGTCCCTGTGNNCATCATTGATGTCAGAGG

FIG. 4B

```
                                      190        200        210        220        230        240
                                       |          |          |          |          |          |
[020384] 020384.As...     CCACAGAGTCGTATGTTTTTCACAATCATAGTAATgCTGATTTTCACAGwATCCAAGAGA

[555403] 555403  -->      CCACAGAGTCGTATGTTTTTCACAATCATAGTAATNCTGATTTTCACAGAATCCAAGAGA
[020384] 020384  -->      CCACAGAGTCGTATGTTTTTCACAATCATAGTAATgCTGATTTTCACAGTATCCAAGAGA 250        260        270        280        290        300
                                       |          |          |          |          |          |
[020384] 020384.As...     AAACTGGAAAATGATTTGGGTCCCTGTGACCATCATTnATGTCAGAGGnCATAGTTAATTT

[555403] 555403  -->      AAANTGGAAATG
[020384] 020384  -->      AAACTGGAAAATGATTTGGGTCCCTGTGACCATCATTNATGTCAGAGGNCATAGTTAATTT 310        320
                                       |          |
[020384] 020384.As...     GCAGGAGAnCAAAAATCAAAA

[020384] 020384  -->      GCAGGAGANCAAAAATCAAAA
```

FIG. 5B

```
                 1                                                    50
PROT.PANC1A   VRR*GLXPRF *EVGF*SLQT SALVLSPLXF HLHRGSCLPK RRFYWEVKVN
  PROT.XS7    ......DPRV R..GF*SLQT SALVLSPLFF HLHRGSCLPK RRFYWEVKVN
PROT.PANC1B   .......... .EVCYXDSER WAFSPSRPRL ....*CCL.. .......XF

51    **                                            100
PROT.PANC1A   A*G*SKMSYG EIXGKFLGPR EEVTSEPRCK KLKSTTESYV FHNHSNADFH
  PROT.XS7    A*G*SKMSYG EIEGKFLGPR EE........ .......... .HNHSNADFH
PROT.PANC1B   SFTFTEMSYG EIEGKFLGPX EEVTSEPRCK KLKSTTESYV FHNHSNADFH 101                                                 150
PROT.PANC1A   XIQEKTGNDW VPVXIIDVRG HSYL...... .......... ..........
  PROT.XS7    RIQEKTGNDW VPVTIIDVRG HSYLQENKIK TTDLHRPLHD EMPGNRPDVI
PROT.PANC1B   XIQEKTGNDW VPVTIIDVRG HSVLQEXKIK .......... ..........

151      162
PROT.PANC1A   .......... ..
  PROT.XS7    ESIDSQVLQE AR
PROT.PANC1B   .......... ..
```

FIG. 7

>496071    LENGTH = 352

PLUS STRAND HSPS:

SCORE = 1000 (276.3 BITS), EXPECT = 1.5E-74, P = 1.5E-74
IDENTITIES = 204/209 (97%), POSITIVES = 204/209 (97%), STRAND = PLUS

```
QUERY:  3949  TCAGATGTCTTATGGTGAAATTGAAGGTAAATTCTTGGGACCTAGAGAAGAAGTAACGAG  4008
              ||||||||||||||||||||||||||||||||||||||||||||||||||||||| |||
SBJCT:   144  TAAGATGTCTTATGGTGAAATTGAAGGTAAATTCTTGGGACCTAGAGAAGAAGTAANGAG   203

QUERY:  4009  TGAGCCACGCTGTAAAAAATTGAAGTCAACCACAGAGTCGTATGTTTTCACAATCATAG  4068
              ||||||||||||||||||||||||||||||||||||||||||||||||||||||||||
SBJCT:   204  TGAGCCACGCTGTAAAAAATTGAAGTCAACCACAGAGTCGTATGTTTTCACAATCATAG   263

QUERY:  4069  TAATGCTGATTTTCACAGAATCCAAGAGAAAACTGGAAATGATTGGGTCCCTGTGACCAT  4128
              |||||||||||||||||||||||| |||||||||||||||||||||||||||||||||
SBJCT:   264  TAATGCTGATTTTCACAGNATCCAAGAGAAAACTGGAAATGATTGGGTCCCTGTGNNCAT   323

QUERY:  4129  CATTGATGTCAGAGGACATAGTTATTTGC  4157
              |||||||||||||||||||||||||||||
SBJCT:   324  CATTGATGTCAGAGGACATAGTTATTTGC   352
```

FIG. 8A

SCORE = 732 (202.3 BITS), EXPECT = 5.2E-110, POISSON P(2) = 5.2E-110
IDENTITIES = 148/150 (98%), POSITIVES = 148/150 (98%), STRAND = PLUS

```
QUERY: 2216 CCGCGATTCTGAGAGGTGGGCTTTTAGTCCCTCCAGACCTCGGCTTTAGTGCTGTCTCCG 2275
             ||||||||||||||||||||||||||||||||||||||||||||||||||||||||||||
SBJCT:    1 CCGCGATTCTGAGAGGTGGGCTTTTAGTCCCTCCAGACCTCGGCTTTAGTGCTGTCTCCG   60

QUERY: 2276 CTTTCTTTCACCTTCACAGAGGTTCGTGTCTTCCTAAAAGAAGGTTTATTGGGAGGTA 2335
             |||||||||||||||||||||||||||||||||||||||||||||||||||||||||||
SBJCT:   61 NTTTCTTTCACCTTCACAGAGGTTCGTGTCTTCCTAAAAGAAGGTTTATTGGGAGGTA  120

QUERY: 2336 AAGGTCAATGCGTAGGGGGTAGAGTAAGGTG 2365
             |||||||||||||||||||||||||||| ||
SBJCT:  121 AAGGTCAATGCGTAGGGGGTAGAGTAAGATG  150
```

FIG. 8B

```
>555403   LENGTH = 252

PLUS STRAND HSPS:

SCORE = 750 (207.2 BITS), EXPECT = 1.3E-53, P = 1.3E-53
IDENTITIES = 154/159 (96%), POSITIVES = 154/159 (96%), STRAND = PLUS

QUERY: 3951 AGATGTCTTATGGTGAAATTGAAGGTAAATTCTTGGGACCTAGAGAAGAAGTAACGAGTG 4010
             ||||||||||||||||||||||||||||||||||||||||||||||||||||||||||||
SBJCT:   94 AGATGTCTTATGGTGAAATTGAAGGTAAATTGAAGGTAAATNNTTGGGACCTAGAGAAGAAGTAACGAGTG 153

QUERY: 4011 AGCCACGCTGTAAAAAATTGAAGTCAACCACAGAGTCGTATGTTTTCACAATCATAGTA 4070
             |||||||||||||||||||||||||||||||||||||||||||||||||||||||||||
SBJCT:  154 AGCCACGCTGTAAAAAATTNAAGTCAACCACAGAGTCGTATGTTTTCACAATCATAGTA 213

QUERY: 4071 ATGCTGATTTTCACAGAATCCAAGAGAAAACTGGAAATG 4109
             || |||||||||||||||||||||||||||| |||||||
SBJCT:  214 ATNCTGATTTTCACAGAATCCAAGAGAAAANTGGAAATG 252

SCORE = 458 (126.6 BITS), EXPECT = 1.1E-62, POISSON P(2) = 1.1E-62
IDENTITIES = 94/97 (96%), POSITIVES = 94/97 (96%), STRAND = PLUS

QUERY: 2203 GTGAGGTTTGTTACCGCGATTCTGAGAGGTGGGCTTTTAGTCCCTCCAGACCTCGGCTTT 2262
             |||||||||||||||| |||||||||||||||||||||||||||||||||||||||||||
SBJCT:    1 GTGAGGTTTGTTACCNCGATTCTGAGAGGTGGGCTTTTAGTCCCTCCAGACCTCGGCTTT 60

QUERY: 2263 AGTGCTGTCTCCGCTTTTCTTTCACCTTCACAGAGGT 2299
             |||||||||||||||| | ||||||||||||||||| |
SBJCT:   61 AGTGCTGTCTCCGATTTTCTTTCACCTTCACAGAGAT 97
```

LENGTH = 271

PLUS STRAND HSPS:

SCORE = 800 (221.1 BITS), EXPECT = 8.5E-58, P = 8.5E-58
IDENTITIES = 164/169 (97%), POSITIVES = 164/169 (97%), STRAND = PLUS

```
QUERY: 3951 AGATGTCTTATGGTGAAATTGAAGGTAAATTCTTGGGACCTAGAGAAGAAGTAACGAGTG 4010
             ||||||||||||||||||||||||||||||||||||||||||||||||||||||||||||
SBJCT:   94 AGATGTCTTATGGTGAAATTGAAGGTAAATTCTTGGGACCTAGTGAAGAAGTAACGAGTG  103

QUERY: 4011 AGCCACGCTGTAAAAAATTGAAGTCAACCACAGAGTCGTATGTTTTCACAATCATAGTA 4070
             |||||||||||||||||||||||||||||||||||||||||||||||||||||||||||
SBJCT:  104 AGCCACGCTGTAAAAAATTGAAGTCAACCACAGAGTCGTATGTTTTCACAATCATAGTA  163

QUERY: 4071 ATGCTGATTTTCACAGAATCCAAGAGAAAACTGGAAATGATTGGGTCCC 4119
             ||||||||||||||| |||||||||||| |||||||||||||| ||||
SBJCT:  164 ATGCTGATTTTCACAGTATCCAAGAGAGAAACTGGAAATGATTTGGGTCC  212
```

FIG. 8D

SCORE = 217 (60.0 BITS), EXPECT = 7.9E-20, POISSON P(2) = 7.9E-20
IDENTITIES = 45/47 (95%), POSITIVES = 45/47 (95%), STRAND = PLUS

QUERY: 2253 CCTCGGGCTTTAGTGCTGTCTCCGCTTTTCTTTCACCTTCACAGAGGT 2299
             ||||||  ||||||||||||||||||||| |||||||||||||||||| |
SBJCT:    1 CCTCGGNTTTAGTGCTGTCTCCGCTTTTCTTTCACCTTCACAGAGAT 47

SCORE = 198 (54.7 BITS), EXPECT = 4.5E-28, POISSON P(3) = 4.5E-28
IDENTITIES = 42/45 (93%), POSITIVES = 42/45 (93%), STRAND = PLUS

QUERY: 4111 TTGGGTCCCTGTGACCATCATTGATGTCAGAGGACATAGTTATTT 4155
             |||||||||||||||||||||||| ||||||||| |||||| ||
SBJCT:  205 TTGGGTCCCTGTGACCATCATTNATGTCAGAGGNCATAGTTAATT 249

LENGTH = 178

PLUS STRAND HSPS:

SCORE = 754 (208.3 BITS), EXPECT = 8.7E-54, P = 8.7E-54
IDENTITIES = 158/167 (94%), POSITIVES = 158/167 (94%), STRAND = PLUS

```
QUERY: 2195 GTACGGGAGGTGAGGTTTGTTACCGCGATTCTGAGAGGTGGGCTTTTAGTCCCTCCAGACC 2254
             ||||||||||||||||||||| ||||||||||||| ||||| |||||||||||||||||||
SBJCT:    1 GTACGGGAGGTGAGGTTTGTNACCGCGATTCTAAGAGGTGGGCTTTTAGTCCCTCCAGACC 60

QUERY: 2255 TCGGCTTTAGTGCTGTGTCTCCGCTTTTCTTTCACCTTCACAGAGGTTCGTGTCTTCCTAAA 2314
             ||||||||||||||||| |||||| ||  ||| ||||||||||||||||| |||| |||| |||
SBJCT:   61 TCGGCTTTAGTGCTGTNTCCNNTTTTTTTCACCTTCACAGAGGTTCGTTNTTCCNAAA 120

QUERY: 2315 AGAAGGTTTTATTGGGAGGTAAAGGTCAATGCGTAGGGGTAGAGTAA 2361
             ||||||||||||||||||||||||||||||||||||||||||||||||
SBJCT:  121 AGAAGGTTTTATTGGGAGGTAAAGGTCAATGCGTAGGGGTAGAGTAA 167
```

LENGTH = 213

PLUS STRAND HSPS:

SCORE = 685 (189.3 BITS), EXPECT = 4.0E-48, P = 4.0E-48
IDENTITIES = 141/146 (96%), POSITIVES = 141/146 (96%), STRAND = PLUS

```
QUERY: 2220 GATTCTGAGAGGTGGGCTTTTAGTCCCTCCAGACCTCGGCTTTAGTGCTGTCTCCGCTTT 2279
             |||||||||||||||||||||||||||  ||||||||||||||||||||||||||||||
SBJCT:    6 GATTCTAAGAGAGTGGGCTTTNAGTCCCTCCANACCTCGGCTTTAGTGCTGTCTCCGCTTT 65

QUERY: 2280 TCTTTCACCTTCACAGAGGTTCGTGTCTTCCTAAAAGAAGGTTTTATTGGGAGGTAAAGG 2339
             | ||||||||||||||||||||||||||||||||||||||||||||||||||||||||
SBJCT:   66 TNTTTCACCTTCACAGAGGTTCGTGTCTTCCTAAAAGAAGAGGTTTTATTGGGAGGTAAAGG 125

QUERY: 2340 TCAATGCGTAGGGGTAGAGAGTAAGGTG 2365
             ||||||||||||||||  ||||  ||
SBJCT:  126 TCAATGCGTAGGGGTAGAGTAAGATG 151
```

SCORE = 327 (90.4 BITS), EXPECT = 3.0E-39, POISSON P(2) = 3.0E-39
IDENTITIES = 67/69 (97%), POSITIVES = 67/69 (97%), STRAND = PLUS

```
QUERY: 3949 TCAGATGTCTTATGGTGAAATTGAAGGTAAATTCTTGGGACCTAGAGAAGAAGTAACGAG 4008
             | |||||||||||||||||||||||| |||||||||||||||||||||||||||||||
SBJCT:  145 TAAGATGTCTTATGGTGAAATTAAAGGTAAATTCTTGGGACCTAGAGAAGAAGTAACGAG 204

QUERY: 4009 TGAGCCACG 4017
             |||||||||
SBJCT:  205 TGAGCCACG 213
```

FIG. 8G

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 373 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Pancreatic Cancer
        ( B ) CLONE: PANC1A ( x i ) SEQUENCE DESCRIPTION: SEQ ID NO:1:

```
GTACGGAGGT  GAGGTTTGTN  ACCGCGATTC  TAAGAGGTGG  GCTTTTAGTC  CCTCCAGACC    60
TCGGCTTTAG  TGCTGTCTCC  GCTTTTYTTT  CACCTTCACA  GAGGTTCGTG  TCTTCCTAAA   120
AGAAGGTTTT  ATTGGGAGGT  AAAGGTCAAT  GCGTAGGGGT  AGAGTAAGAT  GTCTTATGGT   180
GAAATTRAAG  GTAAATTCTT  GGGACCTAGA  GAAGAAGTAA  CGAGTGAGCC  ACGCTGTAAA   240
AAATTGAAGT  CAACCACAGA  GTCGTATGTT  TTTCACAATC  ATAGTAATGC  TGATTTTCAC   300
AGNATCCAAG  AGAAAACTGG  AAATGATTGG  GTCCCTGTGN  NCATCATTGA  TGTCAGAGGA   360
CATAGTTATT  TGC                                                         373
```

( 2 ) INFORMATION FOR SEQ ID NO:2:

( i ) SEQUENCE CHARACTERISTICS:
        ( A ) LENGTH: 321 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Pancreatic Cancer
        ( B ) CLONE: PANC1B ( x i ) SEQUENCE DESCRIPTION: SEQ ID NO:2:

```
GTGAGGTTTG  TTACCNCGAT  TCTGAGAGGT  GGGCTTTTAG  TCCCTCCAGA  CCTCGGCTTT    60
AGTGCTGTCT  CCGMTTTTCT  TTCACCTTCA  CAGAGATGTC  TTATGGTGAA  ATTGAAGGTA   120
AATTCTTGGG  ACCTAGWGAA  GAAGTAACGA  GTGAGCCACG  CTGTAAAAAA  TTGAAGTCAA   180
CCACAGAGTC  GTATGTTTTT  CACAATCATA  GTAATGCTGA  TTTTCACAGW  ATCCAAGAGA   240
AAACTGGAAA  TGATTTGGGT  CCCTGTGACC  ATCATTNATG  TCAGAGGNCA  TAGTTAATTT   300
GCAGGAGANC  AAAAATCAAA  A                                               321
```

POLYNUCLEOTIDES PANC1A AND PANC1B ASSOCIATED WITH PANCREATIC CANCER

FIELD OF THE INVENTION

The present invention relates to novel polynucleotide sequences, PANC1A and PANC1B, associated with pancreatic cancer and to the use of PANC1A and PANC1B in the diagnosis and treatment of pancreatic cancer.

BACKGROUND OF THE INVENTION

The pancreas is an elongated organ which lies behind and below the stomach and above the first loop of the duodenum. It weighs approximately 100 grams and consists of both exocrine and endocrine tissues. The exocrine portion is divided into lobes by connective tissue septa, and each lobe is divided into several lobules. These lobules are composed of grape-like clusters of secretors cells which form sacs known as acini. An acinus is a functional unit, and all acini drain into interlobular ducts which merge to form the main pancreatic duct. It, in turn, joins together with the bile duct from the liver to form the common bile duct that empties into the duodenum. Pancreatic acinar cells make up more than 80% of the total volume of the pancreas and function in the secretion of the various enzymes which assist digestion in the gastrointestinal tract.

The endocrine portion of the pancreas consists of islands of tissues known as islets of Langerhans. These dispersed islets comprise approximately 2% of the total volume of the pancreas. The basic function of the pancreatic endocrine cells is to secrete certain hormones which participate in the metabolism of proteins, carbohydrates, and fats. The hormones secreted by the islets are insulin, glucagon, somatostatin and pancreatic polypeptide.

Carcinoma of the pancreas is the fourth commonest cancer causing death in the United States with an incidence in 1993 of 27,700 and a mortality of 24,500 (Caldas et al, (1994) *Nature Gene* 8:27–32). The disease is more common in males than females and the peak incidence is between the ages of 60 to 70. Incidence of carcinoma of the pancreas is 2 times greater in patients with diabetes mellitus and 2.0 to 2.5 times greater in smokers than non-smokers.

The median survival for individuals subject to pancreatic cancer is six months from the time of diagnosis. Approximately 10% of patients survive one year and the five year survival rate is 1 to 2 percent. (Harrison Principles of Internal Medicine 11th edition, Braunwald et al editors, McGraw-Hill Book Co., New York, pg. 1381–1384.)

Recently, Schutte et al ((1995) *Proc Natl Acad Sci* 92:5950–5954) used the method of representational difference analysis (RDA) as described by (Lisitsyn et al (1995) *Proc Natl Acad Sci* 92:151–155) to demonstrate a homozygous deletion in pancreatic carcinoma mapping to a 1-cM region at 13ql.3. The deletion was flanked by the markers D135171 and D135260 and lay within the 6-cM region identified as containing the $BRCA_2$ (600185) locus of heritable breast cancer susceptibility. Schutte supra suggest that the same gene may be involved in multiple tumor types and that its function is that of a tumor suppressor rather than that of a dominant oncogene. Additionally, Muller-Pillasch et al. submitted to EMBL/GenBank and the gene database of Japan (DDBJ DDBI) in 1994 a nucleotide sequence designated NCBI GI 533948 which was found to be differentially expressed in the pancreatic cancer cell line PATU.

The Sanger Genome Centre (Cambridge, UK) has been involved in a large-scale genomic DNA sequencing project in the region of human chromosome 13 (13q12) thought to contain the gene responsible for Breast Cancer Type 2 (BRCA2). They recently deposited several large fragments of this DNA sequence on their Web Server, in unfinished and unannotated form.

Current methods for the diagnosis of pancreatic cancer include measurement of serum amylase and lipase values, however these values are found to be abnormal in only 10% of all cases. Blood, urine and feces of individuals subject to carcinoma of the body and tail of the pancreas are often normal. Also, standard gastrointestinal x-rays may suggest the presence of carcinoma of the head of the pancreas, but only 50% of all patients with this type of carcinoma have an abnormal examination (Harrison's Principles of Internal Medicine supra).

In view of the difficulty in diagnosing pancreatic cancer, and the low survival rates of individuals subject to pancreatic cancer, it would be advantageous to have an early and accurate method for the detection of pancreatic cancer. It would also be advantageous to provide therapeutic compositions and methods for prevention and treatment of pancreatic cancer.

SUMMARY OF THE INVENTION

The present invention relates to the novel nucleotide sequences, PANC1A (SEQ ID NO: 1) and PANC1B (SEQ ID NO: 2), disclosed herein in FIGS. 1 and 2 and to the use of PANC1A and PANC1B in the diagnosis prevention and treatment of pancreatic cancer.

PANC1A and PANC1B were identified using the ABI Assembler Applications part of the INHERIT™ DNA Analysis System (Applied Biosystems) which creates and manages sequence assembly projects by assembling overlapping sequence fragments into a larger nucleotide sequence. PANC1A and PANC1B were assembled from nucleotide sequences found in normal tissues and were found to have nucleotide homology to nucleotide sequence GI 533948, (human XS7 mRNA) found differentially expressed in a cell line derived from pancreatic adenocarcinoma. As illustrated in FIG. 3, PANC1A contains an exact match to GI 533948 except for an additional 57 bases between 216 and 274 of PANC1A. PANC1B is another variant of GI 533948 which also contains the additional bases but is different from PANC1A.

PANC1A and PANC1B were found to have higher significant nucleotide sequence homology to the Sanger genomic sequences and therefore map to the chromosome region 13q12, see FIG. 8. For the same reason, we have mapped Xs7 to 13q12.

As illustrated in FIG. 4, nucleotide sequence fragments designated 071178 and 180773, derived from placenta, and 496071, derived from hNT-2 cell line (a teratocarcinoma cell line) were assembled to create PANC1A. As illustrated in FIG. 5, nucleotide sequence fragments designated 555403, derived from spinal cord and 020384, derived from inflamed adenoid, were assembled to create PANC1B.

PANC1A and PANC1B show nucleotide sequence homology to Genbank Identifier (GI) 533948, human Xs7, found to be differentially expressed in a pancreatic adenocarcinoma cell line, although GI 533948 was not shown to be mapped or linked to any chromosome. Additionally, Schutte supra demonstrated that a homozygous deletion associated with pancreatic carcinoma mapped to the same region on chromosome 13 as the BRCA2 locus known to be associated with breast cancer susceptibility. Schutte supra suggest that the same gene may be involved in multiple tumor types and may represent a tumor suppressor gene rather than a dominant oncogene.

PANC1A is identical to GI 555403 except for an insertion of an additional 57 nucleotides between nucleotide position 216 and 274 of SEQ ID NO:1, this insertion maintains the reading frame. PANC1B also has homology to GI 555403 but has a different nucleotide sequence than PANC1A.

The variation of PANC1A and PANC1B to Hxs7 may indicate alternative splicing events and possibly a deletion in the pancreatic cancer gene suggested by Schutte supra to be a tumor suppressor and thought to be involved In multiple tumor types. For example, the sequence apparently missing in the Xs7 sequence may alter the activity of the protein, possibly even rendering it inactive.

Nucleotide sequences for PANC1A and PANC1B, or fragments thereof, and amino acid sequences of the polypeptides they encode, will provide the basis for the development of diagnostic methods for the early and accurate detection of pancreatic cancer and other types of cancer, such as for example, breast cancer. For example, nucleotide sequences derived from PANC1A and PANC1B can be used in hybridization assays of biopsied cells and tissues from individuals at risk for or subject to pancreatic cancer or other cancers.

Furthermore, the nucleotide sequences for PANC1A and PANC1B will provide the basis for the development of therapeutics, such as antisense sequences, purified polypeptides and antibodies, for the prevention and treatment of pancreatic cancer. For example, nucleotide sequences derived from PANC1A or PANC1B can be administered to individuals at risk for or subject to pancreatic cancer, or other cancers whose genes map to the same locus, in an attempt to prevent or treat pancreatic cancer.

The polynucleotide sequence disclosed herein for PANC1A and PANC1B, or variants thereof, provide the basis for designing oligonucleotide probes for the diagnosis of disease and conditions associated with pancreatic cancer. Such probes may be used to diagnose cancer before the onset of severe clinical symptoms. The invention also provides for PANC1A and PANC1B antisense molecules which may be used to diminish or eliminate expression of genomic PANC1A and PANC1B nucleotide sequences in individuals at risk for or subject to pancreatic cancer. The present invention also relates, in part, to expression vectors and host cells comprising PANC1A and PANC1B for in vitro or in vivo production of the nucleotide sequences.

The present invention also relates to the use of PANC1A and PANC1B polypeptides, or fragments or variants thereof, thus to produce anti-PANC1A or anti-PANC1B antibodies and to screen for antagonists or inhibitors of PANC1A or PANC1B polypeptides which can be used therapeutically to prevent or treat pancreatic cancer.

The present invention further relates to administration of compositions comprising purified PANC1A or PANC1B polypeptides or variants thereof, to subjects at risk for or subject to pancreatic cancer.

The present invention also relates to compositions comprising anti-PANC1A or PANC1B antibodies, or other antagonists or inhibitors for the diagnosis, prevention or treatment of disease conditions, involving the abnormal expression of PANC1A or PANC1B including pancreatic cancer.

The PANC1A and PANC1B polynucleotide sequences disclosed herein, oligonucleotides, fragments, portions or antisense molecules thereof, may be used in diagnostic assays to detect and quantify levels of PANC1A and PANC1B mRNA in cells and tissues. For example, the PANC1A or PANC1B polynucleotide sequence disclosed herein may be used to detect related or identical sequences in solution-based, membrane-based, or tissue-based assays to diagnose abnormalities in gene expression. The invention further provides diagnostic assays and kits for the detection of PANC1A and PANC1B in cells and tissues comprising purified PANC1A and PANC1B, which may be used as a positive control, and anti-PANC1A and anti-PANC1B antibodies. Such antibodies may be used in solution-based, membrane-based, or tissue-based technologies to detect any disease state or condition related to the expression of PANC1A or PANC1B or expression of deletions or variants thereof.

PANC1A and PANC1B antisense molecules, anti-PANC1A and PANC1B antibodies, antagonists or inhibitors of PANC1A or PANC1B may be used for therapeutic purposes, for example, in inhibiting or neutralizing expression of PANC1A or PANC1B associated with pancreatic cancer. The present invention provides pharmaceutical compositions for the treatment of disease states associated with abnormal expression of PANC1A or PANC1B.

The present invention also encompasses the use of gene therapy methods for the introduction of nucleotide sequences of the present invention into individuals subject to at risk for or pancreatic cancer.

DESCRIPTION OF THE FIGURES

FIG. 1 displays the nucleotide sequence of PANC1A. Sequences shown in this and FIG. 2 were produced using the multisequence alignment program of DNASTAR software (DNASTAR Inc, Madison Wis.).

FIG. 2 displays the nucleotide sequence of PANC1B.

FIG. 3 displays the nucleotide alignment of PANC1A (designated herein as 71178), PANC1B (designated herein as 20483), and GI 533948 (designated as XS7).

FIG. 4(A)–(B) displays the assemblage of PANC1A using clone numbers 71178, 180773 and 496071.

FIG. 5(A)–(B) displays the assemblage of PANC1B using clone numbers 555403 and 020384.

FIG. 7 displays putative amino acid sequence homology between PANC1A, PANC1B and Xs7.

FIGS. 8A–8G display nucleotide homology between the individual nucleotide sequences used in the assembly of PANC1A and PANC1B and the Sanger genomic sequence.

DETAILED DESCRIPTION OF THE INVENTION

Figure 5A:
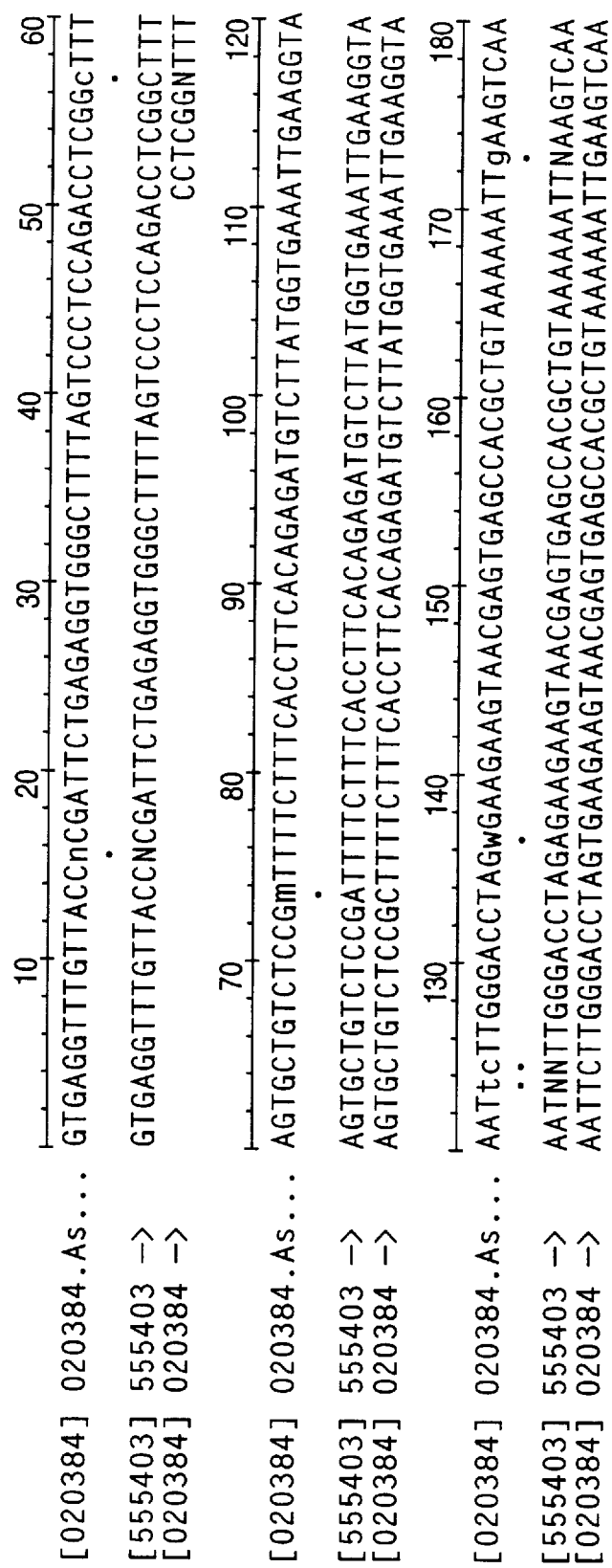

The present invention relates to the novel nucleotide sequences, PANC1A and PANC1B, disclosed herein in FIGS. 1 and 2 and to the use of PANC1A and PANC1B in the diagnosis, prevention, and treatment of pancreatic cancer.

"Nucleic acid sequence" as used herein refers to an oligonucleotide, nucleotide or polynucleotide sequence, and fragments or portions thereof, and to DNA or RNA of genomic or synthetic origin which may be double-stranded or single-stranded whether representing the sense or anti-sense strand. Similarly, "amino acid sequence" as used herein refers to peptide or protein sequences or portions thereof.

As used herein, PANC1A and PANC1B refers to PANC1A and PANC1B from any species, including, bovine, ovine, porcine, equine, murine and preferably human, in naturally occurring or in variant form, or from any source, whether natural, synthetic, semi-synthetic or recombinant.

PANC1A and PANC1B were identified using the ABI Assembler Applications part of the INHERIT™ DNA Analysis System (Applied Biosystems) which creates and manages sequence assembly projects by assembling overlapping sequence fragments into a larger nucleotide sequence. PANC1A and PANC1B were assembled from nucleotide sequences found in normal tissues and were found to have nucleotide homology to nucleotide sequence GI 533948, (human XS7 mRNA) found differentially expressed in a cell line derived from pancreatic adenocarcinoma. As illustrated in FIG. 3, PANC1A contains an exact match to GI 533948 except for an additional 57 bases between 216 and 274 of PANC1A. PANC1B is a variant of GI 533948 which is different from PANC1A. PANC1A and PANC1B were found to have nucleotide sequence homology to the Sanger genomic sequences that map to the chromosome region 13q12.

As used herein, "naturally occurring" refers to a PANC1A and PANC1B with an mRNA sequence found in nature, and "biologically active" refers to an PANC1A and PANC1B having structural, regulatory or biochemical functions of the naturally occurring PANC1A and PANC1B. Likewise, "immunological activity" is defined as the capability of the natural, recombinant or synthetic PANC1A and PANC1B, or any oligopeptide thereof, to induce a specific immune response in appropriate animals or cells and to bind with specific antibodies.

The term "derivative" as used herein refers to the chemical modification of PANC1A and PANC1B. Illustrative of such modifications would be replacement of hydrogen by an alkyl, acyl, or amino group. A PANC1A and PANC1B polypeptide derivative would encode a polypeptide which retains essential biological characteristics of PANC1A and PANC1B.

As used herein, the term "purified" refers to molecules, either nucleic or amino acid sequences, that are removed from their natural environment and isolated or separated from at least one other component with which they are naturally associated.

The PANC1A and PANC1B Coding Sequences

The nucleotide sequence of PANC1A (SEQ ID NO:1) and PANC1B (SEQ ID NO:2) are shown in FIGS. 1 and 2 respectively.

PANC1A and PANC1B show nucleotide sequence homology to GenBank Identifier (GI) 533948, human Xs7, found to be differentially expressed in a pancreatic adenocarcinoma cell line, although GI 533948 was not shown to be mapped or linked to any chromosome. Additionally, Schutte supra demonstrated that a homozygous deletion associated with pancreatic carcinoma mapped to the same region on chromosome 13 as the BRCA2 locus known to be associated with breast cancer susceptibility. Schutte supra suggest that the same gene may be involved in multiple tumor types and may represent a tumor suppressor gene rather than a dominant oncogene.

PANC1A is identical to GI 555403 except for an insertion of an additional 57 nucleotides between nucleotide position 216 and 274 of SEQ ID NO:1, which insertion maintains the reading frame. PANC1B also has homology to GI 555403 but has a different nucleotide sequence than PANC1A.

The variation of PANC1A and PANC1B to Hxs7 may indicate alternative splicing events and possibly a deletion in the pancreatic cancer gene suggested by Schutte supra to be a tumor suppressor and thought to be involved In multiple tumor types.

Methods for DNA sequencing are well known in the art and employ such enzymes as the Klenow fragment of DNA polymerase 1, Sequenase® (US Biochemical Corp, Cleveland Ohio)), Taq polymerase (Perkin Elmer, Foster City Calif.), thermostable T7 polymerase (Amersham, Chicago Ill.), or combinations of recombinant polymerases and proofreading exonucleases such as the ELONGASE Amplification System marketed by Gibco BRL (Gaithersburg Md.) Methods to extend the DNA from an oligonucleotide primer annealed to the DNA template of interest have been developed for both single-stranded and double-stranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; MJ Research, Watertown Mass.) and the Applied Biosystems (Foster City Calif.) Catalyst 800 and 377 and 373 DNA sequencers.

The quality of any particular cDNA library may be determined by performing a pilot scale analysis of the cDNAs and checking for percentages of clones containing vector, lambda or *E. coli* DNA, mitochondrial or repetitive DNA, and clones with exact or homologous matches to public databases.

Extending PANC1A and PANC1B Polynucleotide Sequence

The polynucleotide sequence of PANC1A and PANC1B may be extended utilizing partial nucleotide sequences from SEQ ID NO:1 or SEQ ID NO:2 and various methods known in the art to detect upstream sequences such as promoters and regulatory elements. Gobinda et al (1993; PCR Methods Applic 2:318–22) disclose "restriction-site polymerase chain reaction (PCR)" as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al(1988) Nucleic Acids Res 16:8186). The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR.

Parker JD et al (1991; Nucleic Acids Res 19:3055–60), teach walking PCR, a method for targeted gene walking which permits retrieval of unknown sequence. Promoter-Finder™ a new kit available from Clontech (Palo Alto Calif.) uses PCR, nested primers and PromoterFinder libraries to walk in genomic DNA. This process avoids the need to screen libraries and is useful in finding intron/exon junctions.

Another PCR method, "*Improved Method for Obtaining Full Length cDNA Sequences*" by Guegler et al, patent application Ser. No 08/487,112, filed Jun. 7, 1995 and hereby incorporated by reference, employs XL-PCR™ (Perkin-Elmer, Foster City Calif.) to amplify and/or extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for obtaining introns and extending 5' sequence.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–8).

Expression of PANC1A and PANC1B

In accordance with the present invention, PANC1A and PANC1B polynucleotide sequences which encode PANC1A and PANC1B polynucleotide sequences, fragments, fusion proteins or functional equivalents thereof, may be used to generate recombinant DNA molecules that direct the expression of PANC1A and PANC1B in appropriate host cells. Due to the inherent degeneracy of the genetic code, DNA sequences other than the nucleotide sequences of SEQ ID NO:1 or SEQ ID NO:2 which encode substantially the same or a functionally equivalent amino acid sequence, may be used to clone and express PANC1A and PANC1B, respectively. As will be understood by those of skill in the art, it may be advantageous to produce PANC1A and PANC1B-encoding nucleotide sequences possessing non-naturally occurring codons. Codons preferred by a particular prokaryotic or eukaryotic host (Murray E et al (1989) Nuc Acids Res 17:477–498) can be selected, for example, to increase the rate of PANC1A and PANC1B expression or to produce recombinant RNA transcripts having desirable properties, such as a longer half-life, than transcripts produced from naturally occurring sequence.

Also included within the scope of the present invention are polynucleotide sequences that are capable of hybridizing to SEQ ID NO:1 or SEQ ID NO:2 under conditions of intermediate to maximal stringency. Hybridization conditions are based on the melting temperature (Tm) of the nucleic acid binding complex, as taught in Wahl GM et al. (1987, Methods Enzymol 152:399–407) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein refers to "the process by which a strand of nucleic acid joins with a complementary strand through base pairing" (Coombs J (1994) *Dictionary of Biotechnology,* Stockton Press, New York N.Y.). Amplification as carried out in polymerase chain reaction technologies is described in Dieffenbach CW and GS Dveksler (1995, *PCR Primer, a Laboratory Manual,* Cold Spring Harbor Press, Plainview N.Y.) and incorporated herein by reference.

As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring PANC1A and PANC1B.

As used herein "substitution" results from the replacement of one or more nucleotides or amino acids by different nucleotides or amino acids, respectively.

Variant PANC1A and PANC1B polynucleotide sequences may be used in accordance with the invention and include deletions, insertions or substitutions of different nucleotide residues resulting in a polynucleotide that encodes the same or a functionally equivalent PANC1A and PANC1B polypeptide. Variant PANC1A and PANC1B protein may also be used in accordance with the invention and may include deletions, insertions or substitutions of amino acid residues as long as the result is a functionally equivalent PANC1A and PANC1B. Amino acid substitutions may be made on the basis of similarity in polarity, charge, solubility, hydrophobicity, hydrophilicity, and/or the amphipathic nature of the residues as long as the biological activity of PANC1A and PANC1B is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of PANC1A and PANC1B. As used herein, an "allele" or "allelic sequence" is an alternative form of PANC1A and PANC1B. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of nucleic acids. Each of these types of changes may occur alone, or in combination with the others, one or more times in a given sequence.

The nucleotide sequences of the present invention may be engineered in order to alter a PANC1A and PANC1B coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, etc.

In another embodiment of the invention, a PANC1A and PANC1B natural, modified or recombinant sequence may be ligated to a heterologous sequence to encode a fusion protein. For example, for screening of peptide libraries for inhibitors of PANC1A and PANC1B activity, it may be useful to encode a chimeric PANC1A and PANC1B protein expressing a heterologous epitope that is recognized by a commercially available antibody. A fusion protein may also be engineered to contain a cleavage site located between a PANC1A and PANC1B sequence and the heterologous protein sequence, so that the PANC1A and PANC1B may be cleaved and purified away from the heterologous moiety.

In an alternate embodiment of the invention, the coding sequence of PANC1A and PANC1B could be synthesized, whole or in part, using chemical methods well known in the art (See Caruthers et al (1980) Nuc Acids Res Symp Ser 7:215–233; Crea and Horn (1980) Nuc Acids Res 9:2331; Matteucci and Caruthers (1980) Tetrahedron Lett 21:719; and Chow and Kempe (1981) Nuc Acids Res 9:2807–2817). Alternatively, the protein itself could be produced using chemical methods to synthesize a PANC1A and PANC1B amino acid sequence, whole or in part. For example, peptides can be synthesized by solid phase techniques, cleaved from the resin, and purified by preparative high performance liquid chromatography (eg, Creighton (1983) *Proteins Structures And Molecular Principles,* WH Freeman and Co, New York N.Y.). The composition of the synthetic peptides may be confirmed by amino acid analysis or sequencing (eg, the Edman degradation procedure; Creighton, supra)

Direct peptide synthesis can be performed using various solid-phase techniques (Roberge JY et al (1995) Science 269:202–204) and automated synthesis may be achieved, for example, using Applied Biosystems 431A Peptide Synthesizer in accordance with the instructions provided by the manufacturer. Additionally the amino acid sequence of PANC1A and PANC1B, or any part thereof, may be altered during direct synthesis and/or combined using chemical methods with other cytokine sequences, or any part thereof, to produce a variant polypeptide.

Expression Systems

In order to express a biologically active PANC1A and PANC1B, the nucleotide sequence coding for PANC1A and PANC1B, or a functional equivalent, is inserted into an appropriate expression vector, ie, a vector which contains the necessary elements for the transcription and translation of the inserted coding sequence.

Methods which are well known to those skilled in the art can be used to construct expression vectors containing a PANC1A and PANC1B coding sequence and appropriate transcriptional or translational controls. These methods include in vitro recombinant DNA techniques, synthetic techniques and in vivo recombination or genetic recombination. Such techniques are described in Maniatis et al (1989) *Molecular Cloning, A Laboratory Manual,* Cold Spring Harbor Press, Plainview N.Y. and Ausubel FM et al. (1989) *Current Protocols in Molecular Biology,* John Wiley & Sons, New York N.Y.

A variety of expression vector/host systems may be utilized to contain and express a PANC1A and PANC1B coding sequence. These include but are not limited to bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of PANC1A and PANC1B, vectors based on SV40 or EBV may be used with an appropriate selectable marker.

In bacterial systems, a number of expression vectors may be selected depending upon the use intended for PANC1A and PANC1B. For example, when large quantities of PANC1A and PANC1B are needed for the induction of antibodies, vectors which direct high level expression of fusion proteins that are readily purified may be desirable. Such vectors include, but are not limited to, the *E. coli* cloning and expression vector Bluescript® (Stratagene), in which the PANC1A and PANC1B coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae.* a number of vectors containing constitutive or inducible promoters such as alpha factor, alcohol oxidase and PGH may be used. For reviews, see Ausubel et al (supra) and Grant et al (1987) Methods Enzymol 153:516–544.

In cases where plant expression vectors are used, the expression of an PANC1A and PANC1B coding sequence may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987, EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi RM (1991)

Results Probl Cell Differ 17:85–105) may be used. These constructs can be introduced into plant cells by direct DNA transformation or pathogen-mediated transfection. For reviews of such techniques, see Hobbs S or Murry LE in McGraw Yearbook of Science and Technology (1992) McGraw Hill New York N.Y., pp 191–196 or Weissbach and Weissbach (1988) Methods for Plant Molecular Biology, Academic Press, New York N.Y., pp 421–463.

An alternative expression system which could be used to express PANC1A and PANC1B is an insect system. In one such system, Autographa californica nuclear polyhedrosis virus (AcNPV) is used as a vector to express foreign genes in Spodoptera frugiperda cells or in Trichoplusia larvae. The PANC1A and PANC1B coding sequence may be cloned into a non-essential region of the virus, such as the polyhedrin gene, and placed under control of the polyhedrin promoter. Successful insertion of PANC1A and PANC1B will render the polyhedrin gene inactive and produce recombinant virus lacking coat protein coat. The recombinant viruses are then used to infect S. frugiperda cells or Trichoplusia larvae in which PANC1A and PANC1B is expressed (Smith et al (1983) J Virol 46:584; Engelhard EK et al (1994) Proc Nat Acad Sci 91:3224–7).

In mammalian host cells, a number of viral-based expression systems may be utilized. In cases where a adenovirus is used as a expression vector, a PANC1A and PANC1B coding sequence may be ligated into an adenovirus transcription/ translation complex consisting of the late promoter and tripartite leader sequence. Insertion in a non-essential E1 or E3 region of the viral genome will result in a viable virus capable of expressing PANC1A and PANC1B in infected host cells. (Logan and Shenk (1984) Proc Natl Acad Sci 81:3655–3659). In addition, transcription enhancers, such as the rous sarcoma virus (RSV) enhancer, may be used to increase expression in mammalian host cells.

Specific initiation signals may also be required for efficient translation of an inserted PANC1A and PANC1B coding sequences. These signals include the ATG initiation codon and adjacent sequences. In cases where PANC1A and PANC1B, its initiation codon and upstream sequences, are inserted into the appropriate expression vector, no additional translational control signals may be needed. However, in cases where only coding sequence, or a portion thereof, is inserted, exogenous transcriptional control signals, including the ATG initiation codon, must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system (Scharf et al (1994) Results Probl Cell Differ 20:125–62; Bittner et al (1987) Methods Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a precursor form of the protein may also be important for correct insertion, folding and/or function. Different host cells such as CHO, HeLa, MDCK, 293, W138, etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express PANC1A and PANC1B may be transformed using expression vectors which contain viral origins of replication or endogenous expression elements and a selectable marker gene. Following the introduction of the vector, cells may be allowed to grow for 1–2 days in an enriched media, before they are switched to selective media. The selectable marker confers resistance to selection and allows identification of cells which have stably integrated the introduced sequences into their DNA. Resistant clumps of cells can be proliferated using tissue culture techniques appropriate to the cell type.

Any number of selection systems may be used to recover transformed cell line. These include, but are not limited to, the herpes simplex virus thymidine kinase (Wigler et al (1977) Cell 11:223) and adenine phosphoribosyltransferase (Lowy et al (1980) Cell 22:817) genes which can be employed in tk$^-$ or aprt$^-$ cells, respectively. Also, antimetabolite antibiotic or herbicide resistance can be used as the basis of selection; for example, dhfr confers resistance to methotrexate (Wigler et al (1980) Natl Acad Sci 77:3567); npt, which confers resistance to the aminoglycosides, neomycin and G-418 (Colberre-Garapin et al (1981) J Mol Biol 150:1), and als or pat, which confer resistance to chlorsulfuron and phosphinotricin acetyltransferase (Murry, supra). Additional selectable genes have been described, for example, trpB, which allows cells to utilize indole in place of tryptophan, or hisD, which allows cells to utilize histinol in place of histidine (Hartman and Mulligan (1988) Proc Natl Acad Sci 85:8047). Recently, the use of visible markers has gained popularity with such markers as β glucuronidase, anthocyanin, and luciferin being widely used not only to identify transformants, but also to quantify the amount of transient or stable protein expression attributable to a specific vector system (Rhodes Calif. et al. (1995) Methods Mol Biol 55:121–31).

Identification of Transformants Containing PANC1A and PANC1B

Although the presence/absence of marker gene expression suggests that the gene of interest is also present, its presence and expression should be confirmed. For example, if the PANC1A and PANC1B is inserted within a marker gene sequence, recombinant cells containing PANC1A and PANC1B can be identified by the absence of marker gene function. Alternatively, a marker gene can be placed in tandem with a PANC1A and PANC1B sequence under the control of a single promoter. Expression of the marker gene in response to induction or selection usually indicates expression of PANC1A and PANC1B as well.

Alternatively, host cells which contain the coding sequence for PANC1A and PANC1B and express PANC1A and PANC1B may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the PANC1A and PANC1B polynucleotide sequence can be detected by DNA-DNA or DNA-RNA hybridization or amplification using probes, portions or fragments of PANC1A and PANC1B. Nucleic acid amplification based assays involve the use of oligonucleotides or oligomers based on the PANC1A and PANC1B sequence to detect transformants containing PANC1A and PANC1B DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of PANC1A and PANC1B polypeptide, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on PANC1A and PANC1B polypeptides is preferred, but a competitive binding assay may be employed. These and other assays are described, among other places, in Hampton R et al (1990, *Serological Methods, a Laboratory Manual*, APS Press, St Paul Minn.) and Maddox Del. et al (1983, J Exp Med 158:1211).

A wide variety of labels and conjugation techniques are known by those skilled in the art and can be used in various nucleic and amino acid assays. Means for producing labeled hybridization or PCR probes for detecting sequences related to PANC1A and PANC1B include oligolabeling, nick translation, end-labeling or PCR amplification using a labeled nucleotide. Alternatively, the PANC1A and PANC1B sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

Purification of PANC1A and PANC1B

Host cells transformed with a PANC1A and PANC1B nucleotide sequence may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing PANC1A and PANC1B can be designed with signal sequences which direct secretion of PANC1A and PANC1B through a particular prokaryotic or eukaryotic cell membrane. Other recombinant constructions may join PANC1A and PANC1B to nucleotide sequence encoding a polypeptide domain which will facilitate purification of soluble proteins (Kroll DJ et al (1993) DNA Cell Biol 12:441–53; see also above discussion of vectors containing fusion proteins).

PANC1A and PANC1B may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath J (1992) Protein Expr Purif 3:263–281), protein A domains that allow purification on immobilized immunoglobulin, and the domain utilized in the FLAGS extension/affinity purification system (Immunex Corp, Seattle Wash.). The inclusion of cleavable linker sequences such as Factor XA or enterokinase (Invitrogen, San Diego Calif.) between the purification domain and PANC1A and PANC1B is useful to facilitate purification.

Uses of PANC1A and PANC1B

Figure 6:
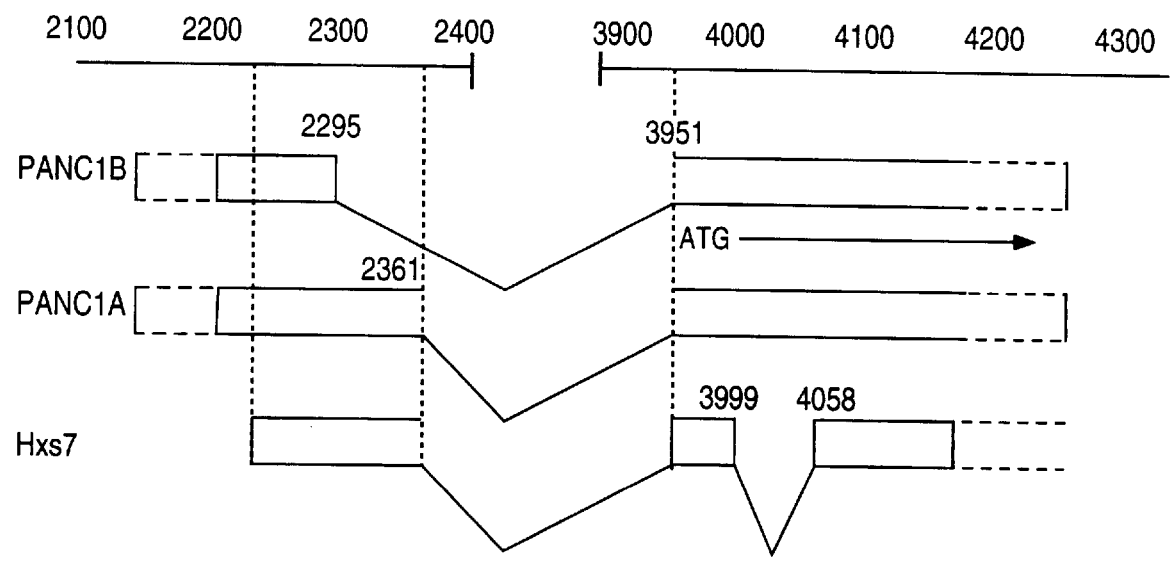
FIG. 6 is a schematic illustration of the alignment of PANC1A, PANC1B and GI 555403 (Hxs7) with the BRAC2 locus.

PANC1A and PANC1B appear to be associated with pancreatic cancer, and possibly other cancers that map to the same locus as the pancreatic cancer gene, eg for example, breast cancer. PANC1A and PANC1B have nucleotide homology with a gene region associated with pancreatic carcinoma that maps to the same region as the BRCA2 locus associated with heritable breast cancer susceptibility, see FIG. 6. PANC1A contains an exact match to GI 533948 except for an additional 57 bases between 216 and 274 of PANC1A. PANC1B is another variant of GI 533948 which also contains the additional bases but is different from PANC1A. Therefore, PANC1A and PANC1B or fragments or derivatives thereof can be used in diagnostic methods for the detection of nucleotide sequences associated with pancreatic cancer, or other cancers, in individuals at risk for or subject to pancreatic cancer or other cancers. Furthermore, nucleotide sequences of PANC1A or PANC1B will provide the basis for therapeutic molecules useful in the treatment of pancreatic cancer, or other related cancers. Additionally, the sequences for PANC1A and PANC1B will provide the basis for screening for compounds that modulate the activity of the gene associated with pancreatic cancer.

In addition, the nontranscribed gene regions flanking the sequences contained within the complete cDNA clones for PANC1A and PANC1B may contain changes which could cause or relate to pancreatic or other types of cancers. Such regions include upstream transcription regulatory sequences such as promoter sequences, CAATT boxes, other regulatory binding sites; introns, and 3' flanking sequences which may contain distal-acting factors such as enhancers. The full transcribed region of the gene will be defined by comparing extended cDNA clone sequences for PANC1A and PANC1B with the sequence of the Sanger gene sequence. Subsequently, such control elements can be identified by similarity to known consensus sequences. The presence of any repeated sequences, such as but not limited to trinucleotide repeats, would constitute other hot spots for relevant mutations.

In another embodiment of the present invention, anti-PANC1A and PANC1B antibodies capable of neutralizing the activity of PANC1A and PANC1B may be used to prevent or treat conditions or disease states such as pancreatic cancer.

Procedures well known in the art may be used for the production of antibodies to PANC1A and PANC1B polypeptides. Such antibodies include, but are not limited to, polyclonal, monoclonal, chimeric, single chain, Fab fragments and fragments produced by a Fab expression library. Neutralizing antibodies, ie, those which inhibit biological activity of PANC1A and PANC1B polypeptides, are especially preferred for diagnostics and therapeutics.

For the production of antibodies, various hosts including goats, rabbits, rats, mice, etc. may be immunized by injection with PANC1A and PANC1B polypeptide or any portion, fragment or oligopeptide which retains immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants which may be employed if purified PANC1A and PANC1B polypeptide is administered to immunologically compromised individuals for the purpose of stimulating systemic defense.

Monoclonal antibodies to PANC1A and PANC1B polypeptide may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy,* Alan R Liss Inc, pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce PANC1A and PANC1B specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for PANC1A and PANC1B may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse WD et al (1989) Science 256:1275–1281).

PANC1A and PANC1B-specific antibodies are useful for the diagnosis of conditions and diseases associated with expression of PANC1A and PANC1B polypeptide. A variety of protocols for competitive binding or immunoradiometric assays using either polyclonal or monoclonal antibodies with established specificities are well known in the art. Such immunoassays typically involve the formation of complexes between PANC1A and PANC1B polypeptides and its specific antibody (or similar PANC1A and PANC1B-binding molecule) and the measurement of complex formation. A two-site, monoclonal-based immunoassay utilizing monoclonal antibodies reactive to two noninterfering epitopes on a specific PANC1A and PANC1B protein is preferred, but a competitive binding assay may also be employed. These assays are described in Maddox Del. et al (1983, J Exp Med 158:1211).

Diagnostic Assays Using PANC1A and PANC1B Specific Antibodies

Anti-PANC1A and PANC1B antibodies are useful for the diagnosis of conditions, disorders or diseases characterized by abnormal expression of PANC1A and PANC1B or expression of genes associated with pancreatic cancer. Diagnostic assays for PANC1A and PANC1B include methods utilizing the antibody and a label to detect PANC1A and PANC1B polypeptide in human body fluids, cells, tissues or sections or extracts of such tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring PANC1A and PANC1B polypeptide, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on PANC1A and PANC1B polypeptide is preferred, but a competitive binding assay may be employed. These assays are described, among other places, in Maddox, Del. et al (1983, J Exp Med 158:1211).

In order to provide a basis for the diagnosis of disease, normal or standard values for PANC1A and PANC1B polypeptide expression must be established. This is accomplished by combining body fluids or cell extracts taken from normal subjects, either animal or human, with antibody to PANC1A and PANC1B polypeptide under conditions suitable for complex formation which are well known in the art. The amount of standard complex formation may be quantified by comparing it with a dilution series of positive controls where a known amount of antibody is combined with known concentrations of purified PANC1A and PANC1B polypeptide. Then, standard values obtained from normal samples may be compared with values obtained from samples from subjects potentially affected by a disorder or disease related to PANC1A and PANC1B polypeptide expression. Deviation between standard and subject values establishes the presence of the disease state.

Drug Screening

PANC1A and PANC1B polypeptide, its immunogenic fragments or oligopeptides can be used for screening therapeutic compounds in any of a variety of drug screening techniques. The fragment employed in such a test may be free in solution, affixed to a solid support, borne on a cell surface, or located intracellularly. The abolition of activity or the formation of binding complexes, between PANC1A and PANC1B polypeptide and the agent being tested, may be measured.

Another technique for drug screening provides for high throughput screening of compounds having suitable binding affinity to the PANC1A and PANC1B polypeptides and is described in detail in Guysen, European Patent Application 84/03564, published on Sep. 13, 1984, incorporated herein by reference. In summary, large numbers of different small peptide test compounds are synthesized on a solid substrate, such as plastic pins or some other surface. The peptide test compounds are reacted with PANC1A and PANC1B fragments and washed. Bound PANC1A and PANC1B is then detected by methods well known in the art. Purified PANC1A and PANC1B can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding PANC1A and PANC1B specifically compete with a test compound for binding PANC1A and PANC1B. In this manner, the antibodies can be used to detect the presence of any peptide which shares one or more antigenic determinants with PANC1A and PANC1B.

Uses of PANC1A and PANC1B Polynucleotide

A PANC1A and PANC1B polynucleotide, or any part thereof, may be used for diagnostic and/or therapeutic purposes. For diagnostic purposes, the PANC1A and PANC1B of this invention may be used to detect and quantitate abnormal gene expression in conditions, disorders or diseases in which PANC1A and PANC1B activity may be implicated, for example pancreatic or breast cancer.

Included in the scope of the invention are oligonucleotide sequences, antisense RNA and DNA molecules and ribozymes, which function to inhibit translation of a PANC1A and PANC1B. Such nucleotide sequences may be used in the treatment of individuals subject to or at risk for pancreatic or breast cancer. Another aspect of the subject invention is to provide for hybridization or PCR probes which are capable of detecting polynucleotide sequences, including genomic sequences, encoding PANC1A and PANC1B or closely related molecules. The specificity of the probe, ie, whether it is derived from a highly conserved, conserved or non-conserved region or domain, and the stringency of the hybridization or amplification (high, intermediate or low) will determine whether the probe identifies only naturally occurring PANC1A and PANC1B, or related sequences. Probes for the detection of related nucleic acid sequences are selected from conserved or highly conserved nucleotide regions of PANC1A and PANC1B and such probes may be used in a pool of degenerate probes. For the detection of identical nucleic acid sequences, or where maximum specificity is desired, nucleic acid probes are selected from non-conserved nucleotide regions or unique regions of PANC1A and PANC1B, such as nucleotide 216 to 274 of PANC1A. As used herein, the term "non-conserved nucleotide region" refers to a nucleotide region that is unique to PANC1A and PANC1B and does not occur in Hxs7.

Diagnostic Uses of PANC1A and PANC1B Polynucleotide

A PANC1A and PANC1B encoding polynucleotide sequence may be used for the diagnosis of diseases resulting from abnormal expression of PANC1A and PANC1B or other genes associated with pancreatic cancer. For example, polynucleotide sequences encoding PANC1A and PANC1B may be used in hybridization or PCR assays of tissues from biopsies or autopsies to detect abnormalities in PANC1A and PANC1B expression. The form of such qualitative or quantitative methods may include Southern or northern analysis, dot blot or other membrane-based technologies; PCR technologies; dip stick, pin or chip technologies; and ELISA or other multiple sample format technologies. All of these techniques are well known in the art, and are in fact the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for PANC1A and PANC1B expression must be established. This is accomplished by combining body fluids or cell extracts taken from normal subjects, either animal or human, with PANC1A and PANC1B or a portion thereof, under conditions suitable for hybridization or amplification. Standard hybridization may be quantified by comparing the values obtained for normal subjects with a dilution series of positive controls run in the same experiment where a known amount of purified PANC1A and PANC1B is used. Standard values obtained from normal samples may be compared with values obtained from samples from subjects potentially affected by a disorder or disease related to PANC1A and PANC1B expression. Deviation between standard and subject values establishes the presence of the disease state.

If disease is established, an existing therapeutic agent is administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

PCR as described in U.S. Pat. Nos. 4,683,195; 4,800,195; and 4,965,188 provides additional uses for oligonucleotides based upon the PANC1A and PANC1B sequence. Such oligomers are generally chemically synthesized, but they may be generated enzymatically or produced from a recombinant source. Oligomers generally comprise two nucleotide sequences, one with sense orientation (5'→3') and one with antisense (3'←5') employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally methods to quantitate the expression of a particular molecule include radiolabeling (Melby PC et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer-of-interest is presented in various dilutions and a spectrophotometric or colorimetric response gives rapid quantitation.

Therapeutic Uses of an PANC1A and PANC1B Polynucleotide

A PANC1A and PANC1B polynucleotide sequence may provide the basis for treatment of various abnormal conditions, including pancreatic or breast cancer.

PANC1A and PANC1B antisense constructs may be useful in the treatment of various abnormal conditions characterized by overexpression of PANC1A and PANC1B or other molecules of the immune system. The successful delivery and expression of such sequences to individuals subject to such diseases will reduce or inhibit the transcription of PANC1A and PANC1B mRNA thereby reducing disease states associated with their expression.

Expression vectors derived from retroviruses, adenovirus, herpes or vaccinia viruses, or from various bacterial plasmids, may be used for delivery of recombinant PANC1A and PANC1B, sense or antisense molecules, to the targeted cell population. Methods which are well known to those skilled in the art can be used to construct recombinant vectors containing PANC1A and PANC1B. See, for example, the techniques described in Maniatis et al (supra)

and Ausubel et al(supra). Alternatively, recombinant PANC1A and PANC1B can be delivered to target cells in liposomes.

The full length cDNA sequence and/or its regulatory elements enable researchers to use PANC1A and PANC1B as a tool in sense (Youssoufian H and HF Lodish 1993 Mol Cell Biol 13:98–104) or antisense (Eguchi et al (1991) Annu Rev Biochem 60:631–652) investigations of gene function. Oligonucleotides, designed from the cDNA or control sequences obtained from the genomic DNA can be used in vitro or in vivo to inhibit expression. Such technology is now well known in the art, and sense or antisense oligonucleotides or larger fragments can be designed from various locations along the coding or control regions.

Additionally, PANC1A and PANC1B expression can be modulated by transfecting a cell or tissue with expression vectors which express high levels of a PANC1A and PANC1B fragment. Such constructs can flood cells with untranslatable sense or antisense sequences. Even in the absence of integration into the DNA, such vectors may continue to transcribe RNA molecules until all copies of the vector are disabled by endogenous nucleases. Such transient expression may last for a month or more with a non-replicating vector (Mettler I, personal communication) and even longer if appropriate replication elements are part of the vector system.

On the other hand, stable transformation of appropriate germ line cells, or preferably a zygote, with a vector containing the PANC1A and PANC1B fragments may produce a transgenic organism (U.S. Pat. No. 4,736,866, 12 Apr. 1988), which produces enough copies of the sense or anti-sense sequence to significantly compromise or entirely eliminate activity of the endogenous PANC1A and PANC1B gene. Frequently, disruption of such genes can be ascertained by observing behaviors such as reduced tumor size.

As mentioned previously, modifications of gene expression can be obtained by designing antisense sequences to the control regions of the PANC1A and PANC1B gene-eg-the promoters, enhancers, and introns. Oligonucleotides derived from the transcription initiation site, eg, between −10 and +10 regions of the leader sequence, are preferred. Antisense RNA and DNA molecules may also be designed to block translation of mRNA by preventing the transcript from binding to ribosomes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of PANC1A and PANC1B RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may also be evaluated by testing accessibility to hybridization with complementary oligonucleotides using ribonuclease protection assays.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

Methods for introducing vectors into cells or tissue include those methods discussed in Section IV of the Examples. In addition, several of these transformation or transfection methods are equally suitable for the ex vivo therapy, the introduction of vectors into stem cells taken from the patient and clonally propagated for autologous transplant as described in U.S. Pat. Nos. 5,399,493 and 5,437,994, disclosed herein by reference.

Furthermore, the PANC1A and PANC1B polynucleotide sequences disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Polynucleotide Sequences Related to PANC1A and PANC1B

The nucleic acid sequence for PANC1A and PANC1B can also be used to generate hybridization probes as previously described, for mapping the endogenous genomic sequence. The sequence may be mapped to a particular chromosome or to a specific region of the chromosome using well known techniques. These include in situ hybridization to chromosomal spreads (Verma et al (1988) *Human Chromosomes: A Manual of Basic Techniques,* Pergamon Press, New York City), flow-sorted chromosomal preparations, or artificial chromosome constructions such as YACs, bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT) has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. between normal, carrier or affected individuals.

Pharmaceutical Compositions

The active compositions of the invention, which may comprise all or portions of PANC1A and PANC1B polypeptides or inhibitors or antagonists, including antibodies, alone or in combination with at least one other agent, such as stabilizing compound, may be administered in any sterile, biocompatible pharmaceutical carrier, including, but not limited to, saline, buffered saline, dextrose, and water.

PANC1A and PANC1B nucleotide and amino acid sequences can be administered to a patient alone, or in combination with other drugs or hormones or in pharmaceutical compositions where it is mixed with excipient(s) or pharmaceutically acceptable carriers. In one embodiment of the present invention, the pharmaceutically acceptable carrier is pharmaceutically inert.

Depending on the condition, disorder or disease being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral, transvaginal, or transmucosal administration; parenteral delivery, including intramuscular, subcutaneous, intramedullary, intrathecal, intraventricular, intravenous, intraperitoneal, or intranasal administration. The preferred route for PANC1A and PANC1B or its inhibitors is intravenous administration.

For injection, the pharmaceutical compositions of the invention may be formulated in aqueous solutions, preferably in physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art.

The pharmaceutical compositions can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. Determination of effective amounts is well within the capability of those skilled in the art, especially in light of the disclosure provided below.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, eg, by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For PANC1A and PANC1B inhibitors, conditions indicated on the label may include treatment of pancreatic cancer.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models to achieve a desirable circulating concentration range that adjusts PANC1A and PANC1B levels.

A therapeutically effective dose refers to that amount of PANC1A and PANC1B or its inhibitor which ameliorates symptoms which may mean decrease in tumor size. Toxicity and therapeutic efficacy of such compounds can be determined by standard pharmaceutical procedures in cell cultures or experimental animals, eg, for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds which exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for PANC1A and PANC1B than for the inhibitors of PANC1A and PANC1B. Administration to the lungs may necessitate delivery in a manner different from that to the kidney, or stomach.

These examples are provided by way of illustration and are not included for the purpose of limiting the invention.

EXAMPLES

I DNA Library Construction

For purposes of discussion, preparation of the inflamed adenoid cDNA library is described. cDNA libraries from placenta, spinal cord, and hNT cell line are prepared by similar methods known to those of skill in the art.

This inflamed adenoid library was constructed from mixed adenoid and tonsil lymphoid tissue surgically removed from a child during a tonsilectomy. The adenoid tissue was obtained from University of California at Los Angeles and frozen for future use. The frozen tissue was ground in a mortar and pestle and lysed immediately in buffer containing guanidinium isothiocyanate (cf Chirgwin JM et al (1979) Biochemistry 18:5294). Lysis was followed by several phenol-chloroform extractions and ethanol precipitations. Poly-A+ mRNA was isolated using biotinylated oligo d(T) and streptavidin coupled to paramagnetic particles (Poly(A) Tract Isolation System; Promega, Madison, Wis.).

The poly A mRNA from the inflamed adenoid tissue was used by Stratagene Inc (11011 N. Torrey Pines Rd., La Jolla, Calif. 92037) to construct a cDNA library. cDNA synthesis was primed using oligo dT and/or random hexamers. Synthetic adapter oligonucleotides were ligated onto cDNA ends enabling its insertion into the UNI-ZAP™ vector system (Stratagene Inc). This allows high efficiency unidirectional (sense orientation) lambda library construction and the convenience of a. plasmid system with blue/white color selection to detect clones with cDNA insertions.

The quality of the each cDNA library was screened using either DNA probes or antibody probes, and then the pBluescript® phagemid (Stratagene Inc) was rapidly excised in living cells. The phagemid allows the use of a plasmid system for easy insert characterization, sequencing, site-directed mutagenesis, the creation of unidirectional deletions and expression of fusion proteins. Phage particles from each library were infected into the E. coli host strain XL1-BLUE® (Stratagene Inc.). The high transformation efficiency of XL1-BLUE increases the probability of obtaining rare, under-represented clones from the cDNA library.

II Isolation and Sequencing of cDNA Clones

Plasmid DNA was released from the cells and purified using the Miniprep Kit (Cat# 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat# 22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 $\mu$l of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer), and the reading frame was determined.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

BLAST, which stands for Basic Local Alignment Search Tool (Altschul SF (1993) J Mol Evol 36:290–300; Altschul, SF et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment: is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

PANC1A and PANC1B were identified using the ABI Assembler Applications part of the INHERIT™ DNA Analysis System (Applied Biosystems) which creates and manages sequence assembly projects by assembling overlapping sequence fragments into a larger nucleotide sequence. PANC1A and PANC1B were assembled from nucleotide sequences found in placenta, spinal cord and hNT cell line and were found to have nucleotide homology to nucleotide sequence GI 533948, (human XS7 mRNA) found differentially expressed in a cell line derived from pancreatic adenocarcinoma.

IV Extension of PANC1A and PANC1B to Recover Regulatory Elements

The nucleic acid sequence of PANC1A and PANC1B may be used to design oligonucleotide primers for obtaining full length sequences from genomic libraries. One primer is synthesized to initiate extension in the antisense direction (XLR) and the other is synthesized to extend sequence in the sense direction (XLF). The primers allowed the known PANC1A and PANC1B sequence to be extended "outward" generating amplicons containing new, unknown nucleotide sequence for the control region of interest. The initial primers may be designed from the cDNA using Oligo 4.0 (National Biosciences Inc, Plymouth Minn.), or another appropriate program, to be 22–30 nucleotides in length, to have a GC content of 50% or more, and to anneal to the target sequence at temperatures about 6°–72° C. Any stretch of nucleotides which would result in hairpin structures and primer-primer dimerizations is avoided.

A human genomic library is used to extend and amplify 5' upstream sequence. If necessary, a second set of primers is designed to further extend the known region. By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |

-continued

| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. The largest products or bands were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

V Labeling of Hybridization Probes

Hybridization probes derived from SEQ ID NO:1 or SEQ ID NO:2 may be employed to screen cDNAs, mRNAs or genomic DNAs. Although the labeling of oligonucleotides, consisting of about 20 base-pairs, is specifically described, essentially the same procedure may be used with larger cDNA fragments. Oligonucleotides are labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are purified with Sephadex G-25 super fine resin column (Pharmacia). A portion containing $10^7$ counts per minute of each is used in a typical membrane based hybridization analysis of human genomic DNA digested with one of the following endonucleases (Ase I, Bgl II, EcoR I, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VI Antisense Molecules

The PANC1A and PANC1B sequence, or any part thereof, may be used to inhibit in vivo or in vitro expression of endogenous PANC1A and PANC1B. Although use of antisense oligonucleotides, consisting of about 20 base-pairs, is specifically described, essentially the same procedure may be used with larger cDNA fragments. An oligonucleotide based on the coding sequence of PANC1A and PANC1B may be used to inhibit expression of endogenous PANC1A and PANC1B. Using Oligo 4.0, the complementary oligonucleotide can be designed from the conserved 5' sequence and used either to inhibit transcription by preventing promoter binding to the upstream nontranslated sequence or translation of an PANC1A and PANC1B transcript by preventing the ribosome from binding to the mRNA.

VII Expression of PANC1A and PANC1B

Expression of the PANC1A and PANC1B is accomplished by subcloning the cDNAs into appropriate vectors and transfecting the vectors into host cells. In this case, pSport or an alternative cDNA cloning vector, pBluescript (Stratagene), is used to express PANC1A and PANC1B in *E. coli*. Upstream of the cloning site, pBluescript contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites. The sequence is cloned into the plasmid using EcoR I and Xho1 sites and the plasmid is used to transfect XL1-BlueMRF' (Stratagene). Induction of the transfected bacterial strain with IPTG using standard methods produces a fusion protein which consists of the first seven residues of β-galactosidase, about 5 to 15 residues of linker, and the full length PANC1A and PANC1B. The signal sequence directs the secretion of PANC1A and PANC1B into the bacterial growth media which can be used directly in the following assay for activity.

Expression of PANC1A and PANC1B as a fusion protein is accomplished by subcloning the cDNA into an expression vector comprising a T7 promoter followed by an initiating methionine codon (ATG), followed by six histidine codons, followed by the TrxA gene of *E. coli* (which encodes thioredoxin) followed by a sequence coding for an enterokinase cleavage site and nucleotide sequence encoding PANC1A and PANC1B or a variant thereof. Expression of PANC1A and PANC1B in such an expression vector allows for purification on IMIAC chromatography (Porath supra).

VIII Production of PANC1A AND PANC1B Specific Antibodies

Although PANC1A and PANC1B purified using PAGE electrophoresis (Maniatis, supra) can be used to immunize rabbits using standard protocols, a monoclonal approach is more commonly employed. The amino acid sequence translated from PANC1A and PANC1B is analyzed using DNASTAR software (DNASTAR Inc) to determine regions of high immunogenicity and a corresponding oligopeptide is synthesized and used to raise antibodies by means known to those of skill in the art. Analysis to select appropriate epitopes, such as those near the C-terminus or in adjacent hydrophilic regions is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel FM et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

IX Purification of PANC1A and PANC1B Using Specific Antibodies

Endogenous or recombinant PANC1A and PANC1B can be purified by immunoaffinity chromatography using antibodies specific for PANC1A and PANC1B. An immunoaffinity column is constructed by covalently coupling PANC1A and PANC1B antibody to an activated chromatographic resin such as CnBr-activated Sepharose (Pharmacia Biotech). After the coupling, the resin is blocked and washed according to the manufacturer's instructions.

Media containing PANC1A and PANC1B is passed over the immunoaffinity column, and the column is washed under conditions that allow the preferential absorbance of PANC1A and PANC1B (eg, high ionic strength buffers in the presence of detergent). The column is eluted under conditions that disrupt antibody/PANC1A and PANC1B binding (eg, a buffer of pH 2–3 or a high concentration of a chaotrope such as urea or thiocyanate ion), and PANC1A and PANC1B is collected.

X Identification of Molecules Which Interact with PANC1A and PANC1B

PANC1A and PANC1B, or biologically active fragments thereof, are labeled with $^{125}$I Bolton-Hunter reagent (Bolton, AE and Hunter, WM (1973) Biochem J 133: 529). Candidate small molecules previously arrayed in the wells of a 96 well plate are incubated with the labeled PANC1A and PANC1B, washed and any wells with labeled PANC1A and PANC1B complex are assayed. Data obtained using different concentrations of PANC1A and PANC1B are used to calculate values for the number, affinity, and association of PANC1A and PANC1B with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A purified polynucleotide consisting of SEQ ID NO:1.

2. A purified polynucleotide consisting of SEQ ID NO:2.

3. An antisense molecule consisting of the complement of the polynucleotide of claim 1 or a portion thereof which specifically hybridizes to PANC1A.

4. An antisense molecule consisting of the complement of the polynucleotide of claim 2 or a portion thereof which specifically hybridizes to PANC1B.

5. An expression vector consisting of the polynucleotide of claim 1 operatively linked to heterologous vector sequences.

6. An expression vector consisting of the polynucleotide of claim 2 operatively linked to heterologous vector sequences.

7. A host cell transformed with the expression vector of claim 5.

8. A host cell transformed with the expression vector of claim 6.

9. A diagnostic composition comprising the polynucleotide of claim 1.

10. A diagnostic composition comprising the polynucleotide of claim 2.

* * * * *